United States Patent [19]
Johnston et al.

[11] Patent Number: 6,042,540
[45] Date of Patent: Mar. 28, 2000

[54] SIDE-LOADING SURGICAL RETRACTOR

[75] Inventors: Terry Johnston, Redwood City; Thomas Wiedenmaier, San Carlos; Daniel Bass, El Granada; Todd Pope, San Francisco, all of Calif.

[73] Assignee: Pacific Surgical Innovations, Inc., San Carlos, Calif.

[21] Appl. No.: 08/912,679

[22] Filed: Aug. 18, 1997

[51] Int. Cl.[7] .................................................. A61B 17/00
[52] U.S. Cl. ........................... 600/213; 600/219; 600/232
[58] Field of Search .................................. 600/201, 210, 600/213, 214, 219, 227, 231, 232

[56] References Cited

U.S. PATENT DOCUMENTS

| | | | |
|---|---|---|---|
| 569,839 | 10/1896 | Roeloffs | 600/213 |
| 4,896,661 | 1/1990 | Bogert et al. | 600/219 X |
| 4,934,352 | 6/1990 | Sullivan, Jr. | 600/213 |
| 5,795,291 | 8/1998 | Koros et al. | 600/213 X |
| 5,846,193 | 12/1998 | Wright | 600/232 X |
| 5,902,233 | 5/1999 | Farley et al. | 600/213 |

FOREIGN PATENT DOCUMENTS

| | | | |
|---|---|---|---|
| 618652 | 9/1935 | Germany | 600/219 |
| 2052998 | 2/1981 | United Kingdom | 600/232 |

*Primary Examiner*—Jeffrey A. Smith
*Attorney, Agent, or Firm*—Wilson Sonsini Goodrich & Rosati

[57] ABSTRACT

A surgical retractor with interchangeable retractor blades allows the retractor blades to be positioned in an incision before being side-loaded into the retractor body and locked in place. The surgical retractor uses a connector head with a circumferential groove that fits in a side-loading socket and is locked in place with a cam that fits in the circumferential groove. A release lever releases the cam and allows the retractor blades to be removed.

29 Claims, 5 Drawing Sheets

SIDE-LOADING SURGICAL RETRACTOR

BACKGROUND OF THE INVENTION

1. Field of the Invention

This invention relates to a surgical retractor with interchangeable retractor blades. More specifically, this invention relates to a surgical retractor with interchangeable retractor blades that can be both side-loading and top-loading.

2. Description of Related Art

Surgical procedures often require the creation of a surgical exposure to allow a surgeon to reach deeper regions of the body. The surgical exposure is usually started with an incision of a suitable depth. Surgical instruments known as retractors are then inserted into the incision and used to pull back skin, muscle, and other soft tissue to permit access to the desired area.

A typical retractor is made up of a retractor body attached to one or more retractor blades. Retractor blades are smooth, thin plates with dull edges that are inserted into the incision to pull back the tissue. Retractor blades come in many different sizes depending on the particular application and physical characteristics of the patient. Retractor blades may be slightly curved or completely flat, and may have end prongs of various configurations to make it easier to pull back tissue. The retractor blades can be attached to a wide variety of retractor bodies, such as for hand-held and self-retaining retractors.

Hand-held retractors are made up of a simple grip attached to a retractor blade. The retractor blade may be fixed or interchangeable. The retractor blade is inserted into the incision, and then the grip is used to pull back the blade to create the surgical exposure. The grip may be attached at an angle to the retractor blade to make it easier to pull back on the blade. Hand-held retractors must be held in place by hand in order to maintain the surgical exposure.

Self-retaining retractors have specialized retractor bodies that allow them to maintain a surgical exposure without needing to be held in place by hand. Two common self-retaining retractors are longitudinal retractors and transverse retractors.

Longitudinal retractors have a retractor body made up of two seesawing arms with a pair of opposed retractor blades on their respective ends. The retractor body typically has a ratcheting mechanism to lock apart the two opposed retractor blades and hold them in place. This maintains the surgical exposure without the need for the retractor to be held in place by hand. The two arms may be hinged to facilitate access to the retraction site. The retractor blades may be either fixed or interchangeable.

Transverse retractors have a retractor body made up of a transverse rack with a fixed arm and a sliding arm. The fixed arm and sliding arm have opposed retractor blades on their respective ends. The sliding arm typically has a turnkey that operates a ratcheting mechanism, which ratchets the sliding arm away from the fixed arm and locks apart the retractor blades. The two arms may be hinged to facilitate access to the retraction site. The retractor blades may be either fixed or interchangeable.

For interchangeable retractor blades, there are several connector designs for allowing the retractor blades to be interchangeably attached to the retractor body. One connector is the top-loading ball snap design, which resembles the mechanism found in common ball-and-socket wrench kits.

The ball snap design uses a top-loading socket which fits over the top of the ball snap. The retractor blades used with the ball snap design typically have a top end bent at a right angle to create a perpendicular section on which the ball snap is mounted.

The ball snap design allows the retractor blades to positively lock into the top-loading socket. This allows the entire retractor to be assembled and handed to the surgeon without the risk of the retractor blades falling off. It also permits the entire retractor to be repositioned in the incision without the risk of the retractor blades becoming detached from the retractor body.

However, many surgeons prefer to position the retractor blades first before attaching the retractor body. Positioning the retractor blades first makes it much easier for the surgeon to create a precise surgical exposure before attaching the retractor body. Pre-positioning of the retractor blades also facilitates the selection of the proper retractor blade length and width.

With the ball snap design, the surgeon must line up the sockets in the retractor body over the tops of the ball snaps before snapping the retractor blades in place. This is a difficult process, as the retractor body arms must be aligned over the ball snaps precisely in order to attach the retractor blades. This alignment process is complicated by the hinged arms and ratcheting mechanisms often found in retractor bodies.

Current side-loading designs attempt to address these problems by making it easier to load the retractor blades into the retractor body after the surgeon has pre-positioned the retractor blades. Current side-loading designs use a post or rail that allow the retractor blades to be loaded from the side. This allows the retractor body to be placed between the retractor blades, and then simply opened up to engage the retractor blades from the side.

However, current side-loading designs do not allow the retractor blades to be positively locked into the retractor body. This means the entire retractor cannot be assembled and then handed to a surgeon without the risk of the retractor blades falling off. The retractor blades are held in place only by the opposing force of the retracted tissue, and may become detached from the retractor body if the surgeon tries to reposition the retractor blades inside the incision. Furthermore, current side-loading designs often misalign, resulting in a poor connection between the retractor blade and the retractor body.

What is needed is a surgical retractor with interchangeable retractor blades, where the retractor body can accept the retractor blades easily without the need for precise alignment, and where the retractor blades can be positively locked into the retractor body.

SUMMARY OF THE INVENTION

One object of the invention is to provide a side-loading surgical retractor.

Another object of the invention is to provide a surgical retractor with interchangeable retractor blades, where the retractor blades are side-loading.

Yet another object of the invention is to provide a surgical retractor with interchangeable retractor blades, where the retractor blades are side-loading and can be locked into the retractor body.

A further object of the invention is to provide a surgical retractor with interchangeable retractor blades, where the retractor blades can be top-loading in addition to side-loading.

Accordingly, the present invention is a retractor apparatus comprising a top-loading ball snap device including a longitudinal axis and a groove formed in an exterior surface of the ball snap device, a holding device including a socket with a receiving opening for receiving at least a portion of the ball snap device, wherein the socket is configured to receive the ball snap device in a lateral direction relative to the ball snap longitudinal axis, and a cam member with a ridge positioned at an exterior surface of the cam member, wherein the cam member is at least partially positioned in the side-loading socket and the ridge is configured to be positioned at least partially in the groove of the ball snap and permit at least a partial rotational movement of the ball snap device relative to the longitudinal axis.

DETAILED DESCRIPTION

Figure 1A:
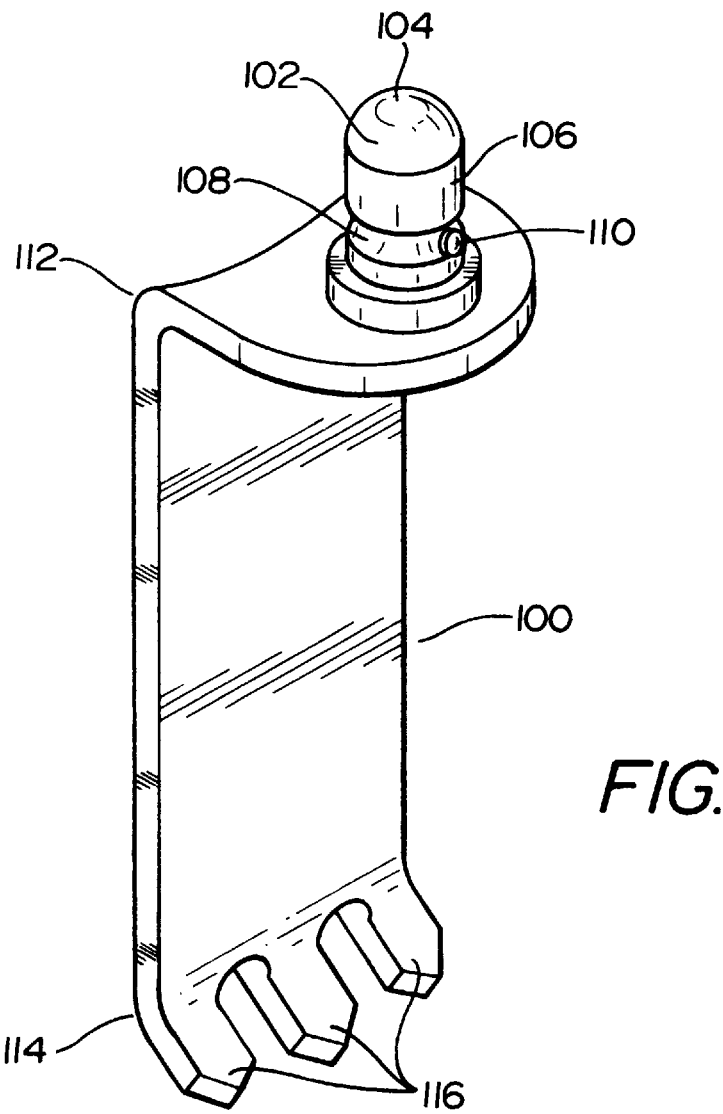
FIG. 1A shows a perspective view of a side-loading retractor blade.
Figure 1B:
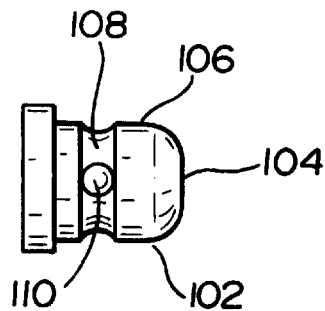
FIG. 1B shows a side view of a side-loading connector head.
Figure 1C:
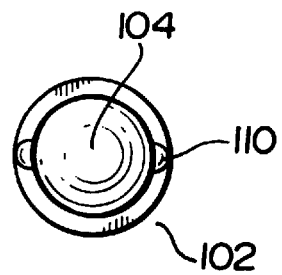
FIG. 1C shows a top view of a side-loading connector head.

FIG. 1A shows a perspective view of a side-loading retractor blade 100 and connector head 102. FIGS. 1B and 1C show a side and top view of connector head 102, respectively. Connector head 102 is generally cylindrical, with a top surface 104 and a side surface 106. Top surface 104 may have rounded edges to facilitate loading of retractor blade 100. Side surface 106 contains a groove 108. Groove 108 may be circumferential around connector head 102. Connector head 102 may have a fixing pin 110.

Side-loading retractor blade 100 may be rectangular or trapezoidal in shape, and may be flat or curved. Side-loading retractor blade 100 may be configured at a right angle near its proximal end 112 where connector head 102 is attached. Side-loading retractor blade 100 has a distal end 114 that may be angled to allow it to reach around and pull back soft tissue. Retractor blade 100 may also contain one or more prongs 116 at its distal end. Prongs 116 may be of different shapes and sizes, depending on the application.

Side-loading retractor blade 100 may be constructed of plastic, ceramic, aluminum, stainless steel, or titanium. A set of side-loading retractor blades may also be color-coded with an anodized finish, for quick selection of the desired size and length.

Figure 2A:
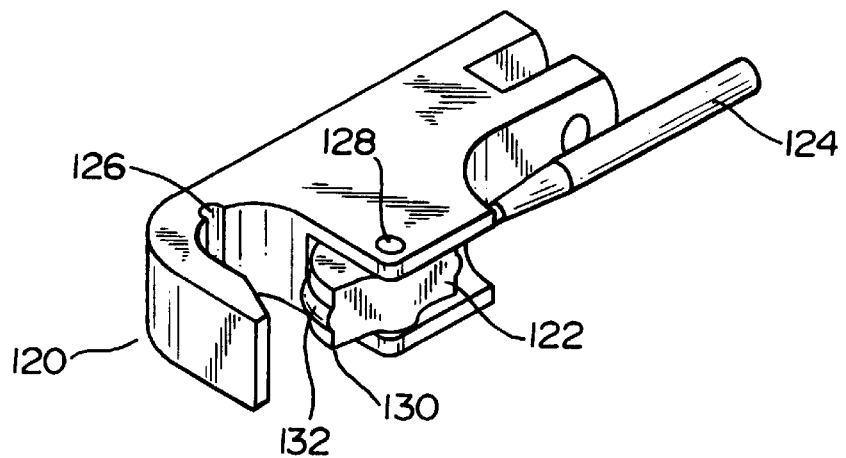
FIG. 2A shows a perspective view of a side-loading socket.

FIG. 2A shows a perspective view of a side-loading socket 120. Side-loading socket 120 is configured to accept connector head 102 from either its top surface 104 or side surface 106. As mentioned earlier, top surface 104 of connector head 102 may have rounded edges to make it easier for connector head 102 to be inserted into side-loading socket 120 from top surface 104.

Side-loading socket 120 may also have a cam 122 configured to fit groove 108 of connector head 102. Cam 122 may be spring-loaded and configured to permit connector head 102 to push cam 122 into an open position and allow connector head 102 to be inserted and fully seated into side-loading socket 120. Once inserted, cam 122 can spring back into a closed position and engage groove 108 to lock connector head 102 in place, and prevent connector head 102 and side-loading retractor blade 100 from falling out of side-loading socket 120.

Cam 122 may be coupled to a release lever 124. Actuation of release lever 124 disengages cam 122 from groove 108 in connector head 102, allowing connector head 102 and retractor blade 100 to be removed from side-loading socket 120.

Cam 122 may be a semi-circular member which rotates about its center 128 held by a pin. Cam 122 contains a holding surface 130 and a ridge 132. Holding surface 130 engages side surface 106 of connector head 102 to provide a snug fit between connector head 102 and side-loading socket 120. Ridge 132 engages groove 108 to prevent connector head 102 and side-loading retractor blade 100 from falling out of side-loading socket 120. Cam 122 is spring-loaded by a spring 134 so that it is biased in the closed position, where cam 122 partially obstructs side-loading socket 120.

Figure 2B:
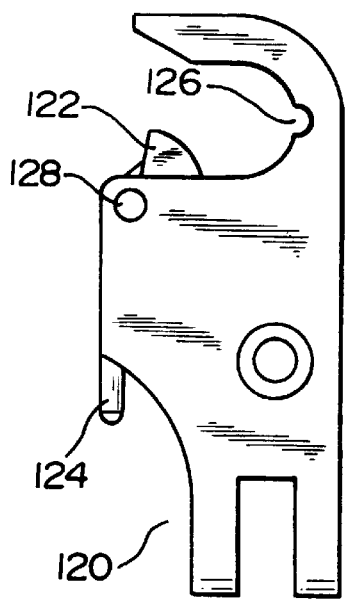
FIG. 2B shows a top view of a side-loading socket in the closed position.
Figure 2C:
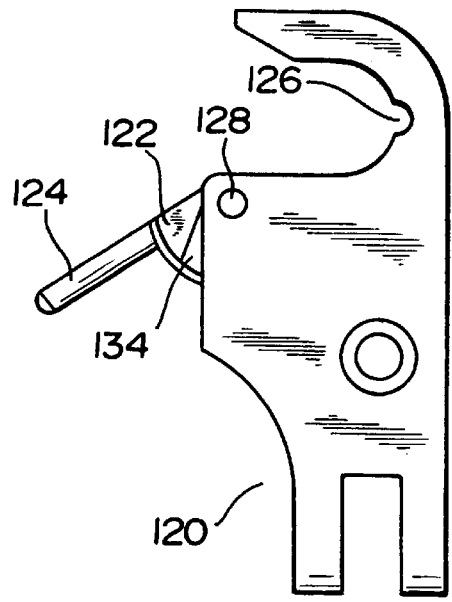
FIG. 2C shows a top view of a side-loading socket in the open position.

Release lever 124 may be a thin rod attached to cam 122. Release lever 124 rotates the semi-circular member so that cam 122 no longer partially obstructs side-loading socket 120, and ridge 132 no longer engages groove 108. This effectively opens side-loading socket 120 and allows connector head 102 to be released from side-loading socket 120. FIGS. 2B and 2C show a top view of side-loading socket 120 in the closed and open positions, respectively. Side-loading socket 120 may also contain a recess 126 configured to receive fixing pin 110 contained in connector head 102. Fixing pin 110, once fitted in recess 126, prevents rotation of connector head 102 and retractor blade 100 in side-loading socket 120.

Side-loading socket 120 may also be configured to be compatible with top-loading ball snap connector designs. Side-loading socket 120 can be manufactured with dimensions capable of receiving top-loading ball snap connectors. Cam 122 can provide a positive lock of ball snap connectors.

Figure 3:
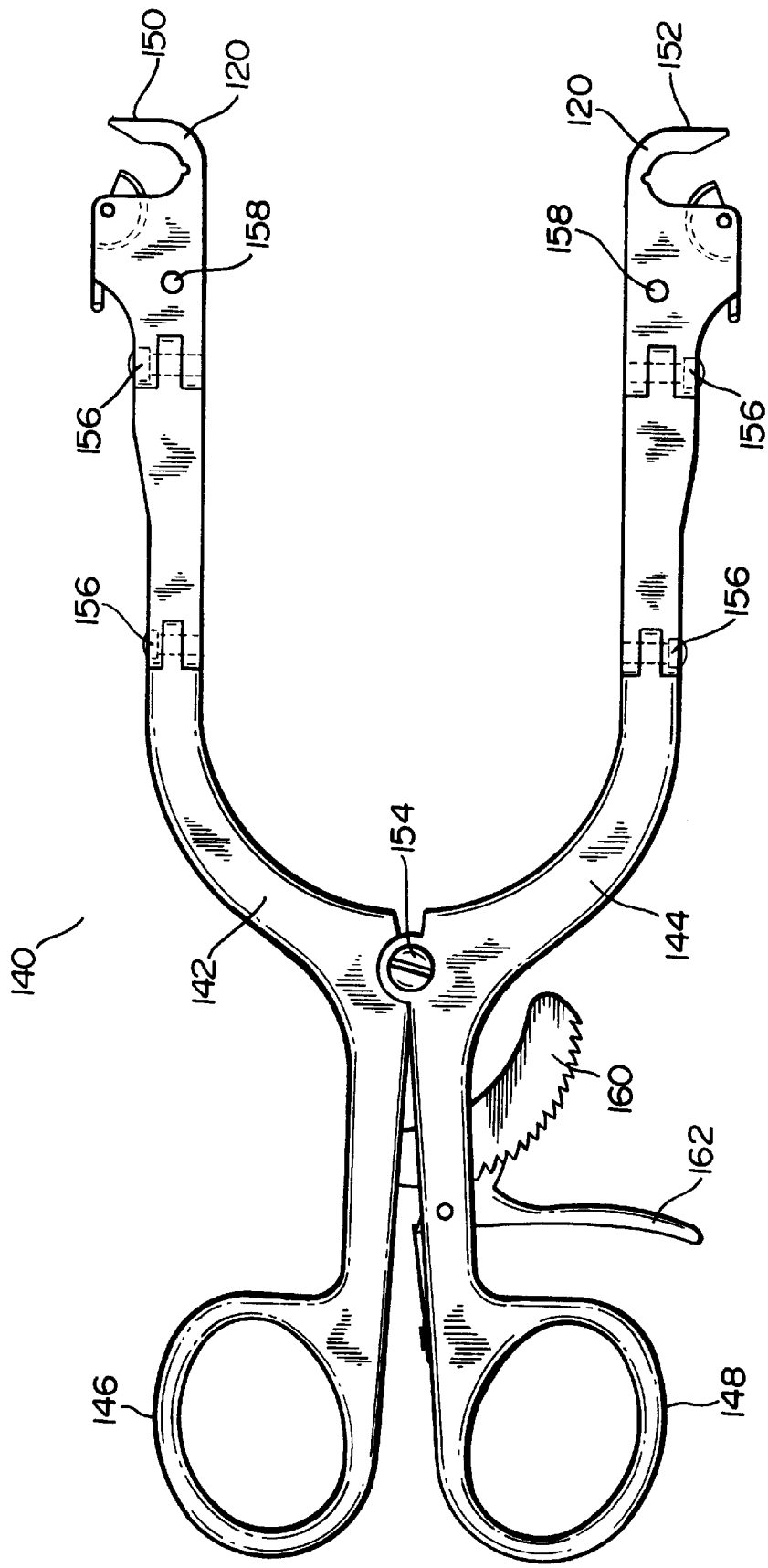
FIG. 3 shows a top view of a side-loading longitudinal retractor.

FIG. 3 is a top view of a side-loading longitudinal retractor 140. Side-loading longitudinal retractor 140 includes two longitudinal retractor arms 142 and 144. Longitudinal retractor arms 142 and 144 have proximal ends 146 and 148 which may contain control ends for receiving a user's fingers. Longitudinal retractor arms 142 and 144 have distal ends 150 and 152, respectively, each of which contains a side-loading socket 120.

Longitudinal retractor arms 142 and 144 are configured to rock on a pivot 154. Retractor arms 142 and 144 may each contain one or more hinges 156. Hinges 156 permit side-loading sockets 120 to be positioned closer to a wound or incision. Longitudinal retractor arms 142 and 144 may each contain suture holes 158. Suture holes 158 permit longitudinal retractor arms 142 and 144 to be sutured in place and help prevent movement of longitudinal retractor 140 after longitudinal retractor 140 has been positioned in a desired location.

Longitudinal retractor 140 may also include a ratcheting mechanism 160 for locking retractor arms 142 and 144 apart in a desired position. Ratcheting mechanism 160 may include a release lever 162, which permits retractor arms 142 and 144 to be unlocked and brought back together again.

Figure 4:
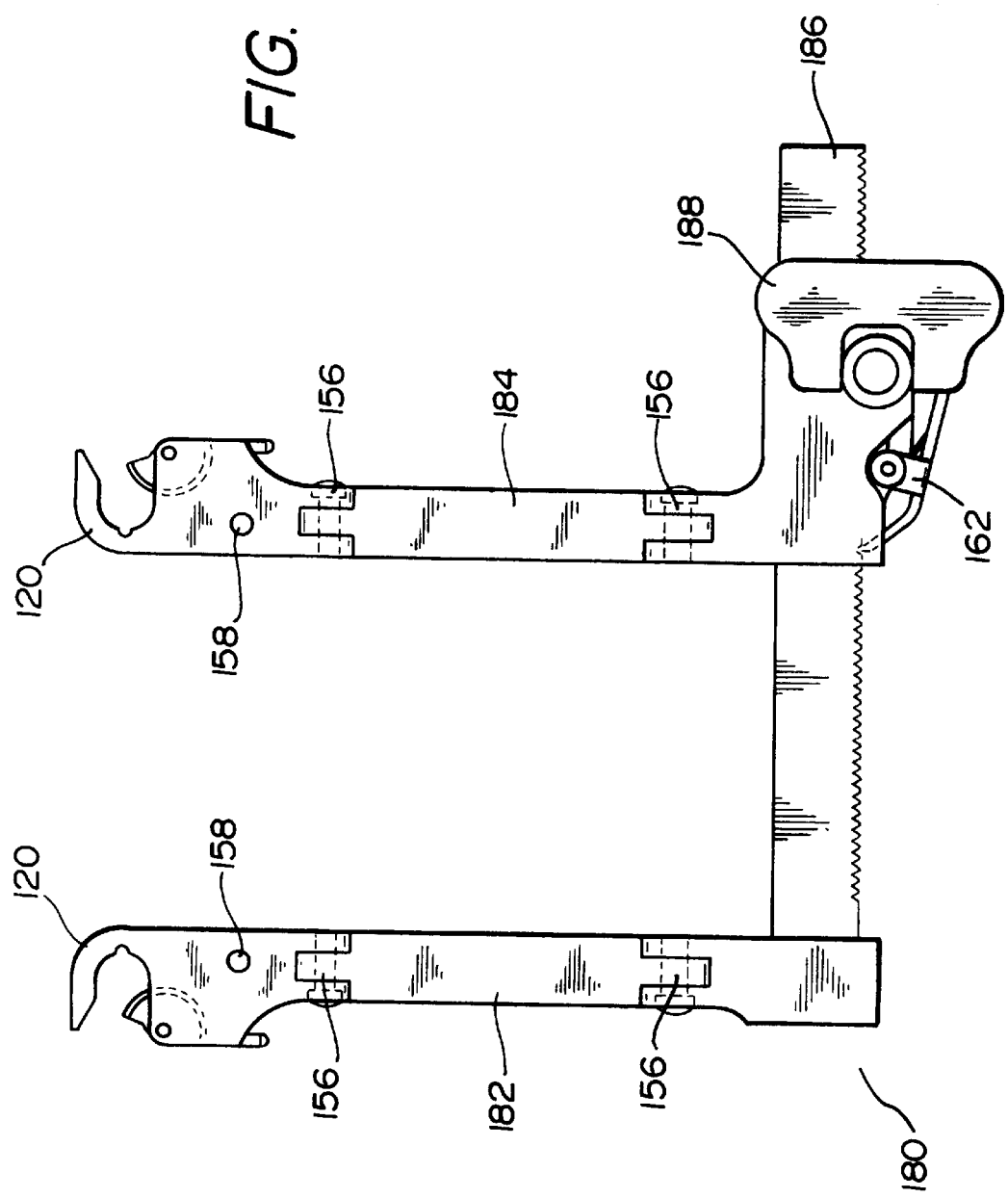
FIG. 4 shows a top view of a side-loading transverse retractor.

FIG. 4 is a top view of a side-loading transverse retractor 180. Side-loading transverse retractor 180 includes a fixed retractor arm 182 and sliding retractor arm 184. Fixed retractor arm 182 and sliding retractor arm 184 each have a side-loading socket 120. Fixed retractor arm 182 and sliding retractor arm 184 may each contain one or more hinges 156 and suture holes 158.

Fixed retractor arm 182 is fixedly mounted to a transverse rack 186. Sliding retractor arm 184 is slidably mounted to transverse rack 186. Sliding retractor arm 184 contains a ratcheting turnkey 188 which allows it to ratchet on transverse rack 186 away from fixed retractor arm 182. Sliding retractor arm 184 may be released by a release lever 162.

Figure 5:
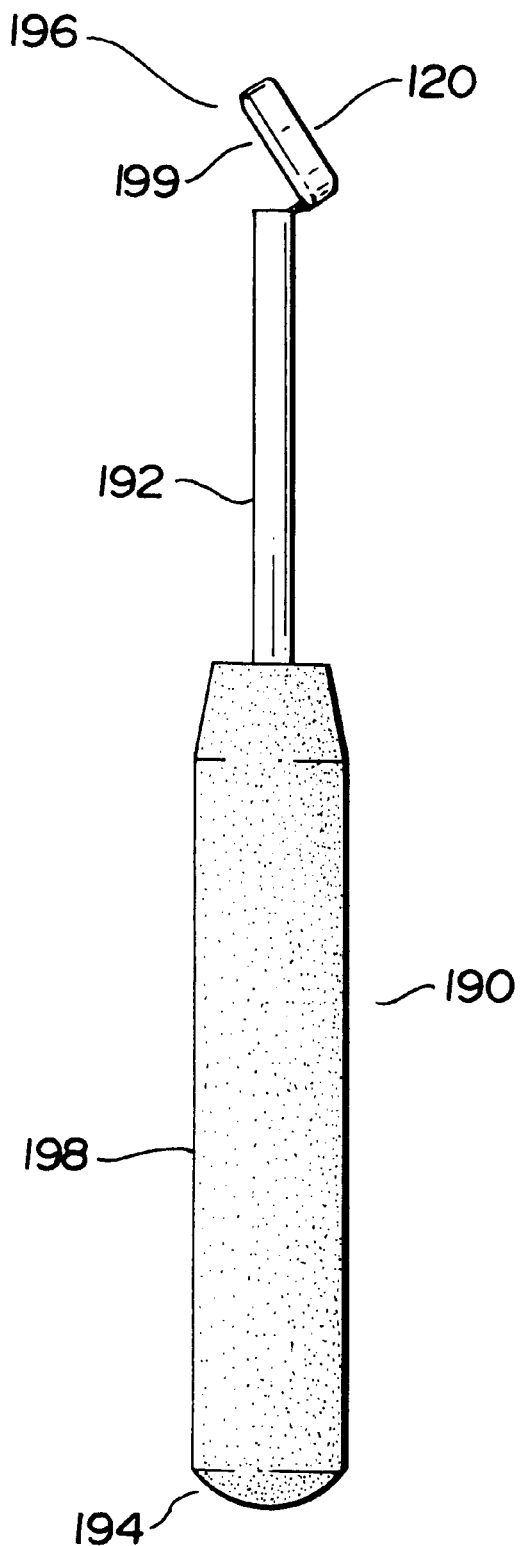
FIG. 5 shows a side-loading hand-held retractor.

FIG. 5 is a side-loading hand-held retractor 190. Side-loading hand-held retractor 190 includes a shaft 192 with a proximal end 194 and a distal end 196. Hand-held retractor 190 includes a side-loading socket 120 at distal end 196.

Hand-held retractor 190 may include a handle 198 at proximal end 194. Hand-held retractor 190 may also include an angled headpiece 199 at distal end 196 coupling shaft 192 to side-loading socket 120. Angled headpiece 199 facilitates access to a wound or incision.

Side-loading longitudinal retractor 140, side-loading transverse retractor 180, and side-loading hand-held retractor 190 may be constructed of plastic, ceramic, aluminum, stainless steel, or titanium.

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

What is claimed is:

1. A retractor apparatus, comprising:
    a top-loading ball snap device including a longitudinal axis and a groove formed in an exterior surface of the ball snap device;
    a holding device including a socket with a receiving opening for receiving at least a portion of the ball snap device, wherein the socket is configured to receive the ball snap device in a lateral direction relative to the ball snap longitudinal axis; and
    a cam member with a ridge positioned at an exterior surface of the cam member, wherein the cam member is at least partially positioned in a side-loading socket and the ridge is configured to be positioned at least partially in the groove of the ball snap and permit at least a partial rotational movement of the ball snap device relative to the longitudinal axis.

2. The apparatus of claim 1, wherein the top-loading ball snap device is coupled to a retractor blade.

3. The apparatus of claim 1, further comprising:
    a release lever coupled to the cam member.

4. The apparatus of claim 3, wherein the cam member sufficiently locks the ball snap device in the socket and prevents the retractor blade from falling away from the holding device.

5. The apparatus of claim 1, wherein the cam member is configured to provide a positive lock of the ball snap device in the socket.

6. The apparatus of claim 1, wherein the cam member significantly eliminates a lateral movement of the ball snap device relative to the holding device.

7. The apparatus of claim 1, wherein the receiving opening is configured to receive the ball snap device in one or two orthogonal directions relative to the longitudinal axis.

8. The apparatus of claim 1, wherein the receiving opening is configured to receive the ball snap device in two different directions relative to the longitudinal axis.

9. The apparatus of claim 1, wherein the ridge and groove are configured to limit a lateral movement of a retractor blade.

10. The apparatus of claim 1, further comprising:
    a transverse retractor coupled to the holding device.

11. The apparatus of claim 10, wherein the first and second arms include a first and a second hinge, respectively.

12. The apparatus of claim 1, further comprising:
    a longitudinal retractor coupled to the holding device.

13. The apparatus of claim 12, wherein the first and second arms include a first and a second hinge, respectively.

14. A surgical retractor, comprising:
    a retractor body having a socket for receiving a connector head, the socket configured to be able to receive the connector head from both a top surface of the connector head and a side surface of the connector head.

15. The surgical retractor of claim 14, wherein the side surface of the connector head includes a groove.

16. The surgical retractor of claim 15, wherein the socket includes a locking device, the locking device configured to be able to engage the groove.

17. The surgical retractor of claim 16, wherein the locking device includes a spring-loaded cam.

18. The surgical retractor of claim 17, wherein the locking device includes a release device coupled to the locking device.

19. The surgical retractor of claim 18, wherein the release device includes a release lever.

20. The surgical retractor of claim 14, wherein the connector head includes a fixing pin.

21. The surgical retractor of claim 20, wherein the socket includes a recess configured to be able to receive the fixing pin.

22. A surgical retractor, comprising:
    a retractor blade having a connector head, the connector head having a top surface and a side surface; and
    a retractor body having a socket, the socket configured to be able to receive the connector head from both the top surface of the connector head and the side surface of the connector head.

23. The surgical retractor of claim 22, wherein the side surface of the connector head includes a groove.

24. The surgical retractor of claim 23, wherein the socket includes a locking device, the locking device configured to be able to engage the groove.

25. The surgical retractor of claim 24, wherein the locking device includes a spring-loaded cam.

26. The surgical retractor of claim 24, wherein the locking device includes a release device coupled to the locking device.

27. The surgical retractor of claim 26, wherein the release device includes a release lever.

28. The surgical retractor of claim 22, wherein the connector head includes a fixing pin.

29. The surgical retractor of claim 28, wherein the socket includes a recess configured to be able to receive the fixing pin.

* * * * *